(12) United States Patent
Wu et al.

(10) Patent No.: US 10,927,182 B2
(45) Date of Patent: Feb. 23, 2021

(54) HUMANIZED BCMA ANTIBODY AND BCMA-CAR-T CELLS

(71) Applicant: Caribou Biosciences, Inc., Berkeley, CA (US)

(72) Inventors: Lijun Wu, Albany, CA (US); Vita Golubovskaya, Richmond, CA (US)

(73) Assignee: Caribou Biosciences, Inc., Berkeley, CA (US)

( * ) Notice: Subject to any disclaimer, the term of this patent is extended or adjusted under 35 U.S.C. 154(b) by 0 days.

(21) Appl. No.: 17/010,798

(22) Filed: Sep. 2, 2020

(65) Prior Publication Data

US 2020/0399387 A1    Dec. 24, 2020

Related U.S. Application Data

(63) Continuation of application No. PCT/US2020/013662, filed on Jan. 15, 2020.

(60) Provisional application No. 62/793,274, filed on Jan. 16, 2019.

(51) Int. Cl.

| | |
|---|---|
| C07K 16/28 | (2006.01) |
| C07K 14/705 | (2006.01) |
| C07K 14/725 | (2006.01) |
| A61K 35/17 | (2015.01) |
| A61P 35/00 | (2006.01) |
| A61K 9/00 | (2006.01) |
| C12N 5/0783 | (2010.01) |
| A61K 39/00 | (2006.01) |
| A61K 38/00 | (2006.01) |
| A61K 35/12 | (2015.01) |

(52) U.S. Cl.
CPC ........ *C07K 16/2878* (2013.01); *A61K 9/0019* (2013.01); *A61K 35/17* (2013.01); *A61P 35/00* (2018.01); *C07K 14/7051* (2013.01); *C07K 14/70517* (2013.01); *C07K 14/70578* (2013.01); *C12N 5/0636* (2013.01); *A61K 38/00* (2013.01); *A61K 2035/124* (2013.01); *A61K 2039/505* (2013.01); *A61K 2039/54* (2013.01); *C07K 2317/24* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2510/00* (2013.01)

(58) Field of Classification Search
None
See application file for complete search history.

(56) References Cited

FOREIGN PATENT DOCUMENTS

| WO | WO2010/104949 | 9/2010 |
|---|---|---|
| WO | WO2013/154760 | 10/2013 |
| WO | WO2016/014565 | 1/2016 |
| WO | WO2017/130223 | 8/2017 |
| WO | WO2017/211900 | 12/2017 |
| WO | WO2019/195017 | 10/2019 |

OTHER PUBLICATIONS

Golubovskaya et al. ("CD47-CAR-T Cells Effectively Kill Target Cancer Cells and Block Pancreatic Tumor Growth." Cancers vol. 9,10 139. Oct. 21, 2017, doi:10.3390/cancers9100139). (Year: 2017).*
"Instructions for Authors," Cancers Journal, retrieved from the Cancers Journal website Dec. 31, 2020, 39 pages. (Year: 2020).*
Ali, S.A., et al., (2016). T cells expressing an anti-B-cell maturation antigen chimeric antigen receptor cause remissions of multiple myeloma. Blood (2016) 128, 1688-1700.
Berahovich, R., et al., FLAG-tagged CD19-specific CAR-T cells eliminate CD19-bearing solid tumor cells in vitro and in vivo. Front Biosci (Landmark Ed)(2017) Jun. 1;22: 1644-1654.
Berahovich, R., et al., CAR-T Cells Based on Novel BCMA Monoclonal Antibody Block Multiple Myeloma Cell Growth. Cancers (2018) 10(9):323.
Bluhm, J., et al., CAR T tCell with enhanced Sensitivity to B Cell Maturation Antigen for the Targeting of B Cell Non-Hodgkins's Lymphoma and Multiple Myeloma. Molecular Therapy (2018) 26:8, 1-15.
Brudno, J., et al., T Cells Genetically Modified to Express an Anti-B-Cell Maturation Antigen Chimeric Antigen Receptor Cause Remissions of Poor-Prognosis Relapsed Multiple Myeloma. J Clin Oncol (2018) 36(22):2267-2280.
Carpenter, R., et al., B-cell maturation antigen is a promising target for adoptive T-cell therapy of multiple myeloma. Clin Cancer Res (2013) 19(8):2048-60.
Cohen, A., et al., B cell maturation antigen-specific CAR T cells are clinically active in multiple myeloma. J Clin Invest (2019)129(6)2210-2221.
D'Agostino, M. and Raje N., Anti-BCMA CAR T-cell therapy in multiple myeloma: can we do better? Leukemia (2020) 34:21-34.
Friedman, K., et al., Effective Targeting of Multiple B-Cell Maturation Antigen—Expressing Hematological Malignances by Anti-B-Cell Maturation Antigen Chimeric Antigen Receptor T Cells. Hum Gene Ther (2018) 29(5):585-601.
Golubovskaya ,V, and Wu L. Different Subsets of T Cells, Memory, Effector Functions, and CAR-T Immunotherapy. Cancers, (2016) 15, 8 (3).

(Continued)

*Primary Examiner* — Zachary S Skelding
(74) *Attorney, Agent, or Firm* — Barbara G. McClung; Katharina F. S. Stengel

(57) ABSTRACT

The present invention is directed to a humanized BCMA single-chain variable fragment (scFv), comprising $V_H$ having the amino acid sequence of SEQ ID NO: 3 and $V_L$ having the amino acid sequence of SEQ ID NO: 5. The present invention is also directed to a BCMA chimeric antigen receptor fusion protein comprising from N-terminus to C-terminus: (i) a single-chain variable fragment (scFv) of the present invention, (ii) a transmembrane domain, (iii) at least one co-stimulatory domains, and (iv) an activating domain. This humanized BCMA-CAR-T cells have specific killing activity against BCMA-positive tumor cells.

18 Claims, 10 Drawing Sheets

Specification includes a Sequence Listing.

(56) References Cited

OTHER PUBLICATIONS

Maus, M.V., et al; T cells expressing chimeric antigen receptors can cause anaphylaxis in humans. Cancer Immunol Res (2013) 1:26-31.
Maus, M.V., et al., Antibody-modified T cells: CARs take the front seat for hematologic malignancies. Blood (2014) 123, 2625-2635.
Pont, M., et al., γ-secretase inhibition increases efficacy of BCMA-specific chimeric antigen receptor T cells in multiple myeloma. Blood (2019) 134(19):1585-1597.
Raje, N., et al., Anti-BCMA CAR T-Cell Therapy bb2121 in Relapsed or Refractory Multiple Myeloma. N Engl J Med (2019) 380(18):1726-1737.
Ramos, C., et al., CAR-T Cell Therapy for Lymphoma. Annu Rev Med (2016); 67:165-83.
Smith, E., et al., Development and Evaluation of an Optimal Human Single-Chain Variable Fragment-Derived BCMA-Targeted CAR T Cell Vector. Mol Ther (2018) 26(6):1447-1456.
Tai, Y.T., and Anderson, K.C. (2015). Targeting B-cell maturation antigen in multiple myeloma. Immunotherapy (2015) 7(11):1187-99.
Xu, J., et al., Exploratory trial of a biepitopic CAR T-targeting B cell maturation antigen in relapsed/refractory multiple myeloma. Proc Natl Acad Sci U S A (2019) 116(19):9543-9551.
PCT Written Opinion of the International Searching Authority for related International Application No. PCT/US2020/013662.
PCT Search Report of the International Searching Authority for related International Application No. PCT/US2020/013662.

* cited by examiner

```
          10         20         30         40         50
MLQMAGQCSQ NEYFDSLLHA CIPCQLRCSS NTPPLTCQRY CNASVTNSVK
          60         70         80         90        100
GTNAILWTCL GLSLIISLAV FVLMFLLRKI NSEPLKDEFK NTGSGLLGMA
         110        120        130        140        150
NIDLEKSRTG DEIILPRGLE YTVEECTCED CIKSKPKVDS DHCFPLPAME
         160        170        180
EGATILVTTK TNDYCKSLPA ALSATEIEKS ISAR
```

HUMANIZED BCMA ANTIBODY AND BCMA-CAR-T CELLS

This application is a continuation under 35 U.S.C. § 111(a) of PCT Application No. PCT/US2020/013662, filed 15 Jan. 2020, now pending, which claims the benefit of and priority to U.S. Provisional Application No. 62/793,274, filed 16 Jan. 2019, now expired, which applications are incorporated herein by reference in their entireties.

REFERENCE TO SEQUENCE LISTING, TABLE OR COMPUTER PROGRAM

The sequences referred to herein are listed in the Sequence Listing submitted as an ASCII text file entitled "CBI038-10_ST25.txt"—16 KB, which was created on 28 Aug. 2020. The Sequence Listing entitled "CBI038-10_ST25.txt" is incorporated herein by reference in its entirety.

FIELD OF THE INVENTION

The present invention relates to humanized BCMA antibody (PMC306) and BCMA-CAR-T cells specifically decreasing multiple myeloma tumor growth, which are useful in the field of adoptive immunity gene therapy for tumors.

BACKGROUND OF THE INVENTION

Immunotherapy is emerging as a highly promising approach for the treatment of cancer. T cells or T lymphocytes, the armed forces of our immune system, constantly look for foreign antigens and discriminate abnormal (cancer or infected cells) from normal cells. Genetically modifying T cells with CAR (Chimeric antigen receptor) constructs is the most common approach to design tumor-specific T cells. CAR-T cells targeting tumor-associated antigens (TAA) can be infused into patients (called adoptive cell transfer or ACT) representing an efficient immunotherapy approach [1, 2]. The advantage of CAR-T technology compared with chemotherapy or antibody is that reprogrammed engineered T cells can proliferate and persist in the patient ("a living drug") [1, 2].

CARs typically consist of a monoclonal antibody-derived single-chain variable fragment (scFv) at the N-terminal part, hinge, transmembrane domain and a number of intracellular co-activation domains: (i) CD28, (ii) CD137 (4-1BB), CD27, or other co-stimulatory domains, in tandem with an activation CD3-zeta domain (FIG. 1). The evolution of CARs went from first generation (with no co-stimulation domains) to second generation (with one co-stimulation domain) to third generation CAR (with several co-stimulation domains). Generating CARs with two costimulatory domains (the so-called $3^{rd}$ generation CAR) have led to increased cytolytic CAR-T cell activity, improved persistence of CAR-T cells leading to its augmented antitumor activity.

BCMA

B cell maturation antigen (BCMA) is a cell surface receptor, also known as CD269 and tumor necrosis factor receptor superfamily member 17 (TNFRSF17), that is encoded by TNFRSF17 gene. This receptor is expressed mainly in mature B lymphocytes and in most cases overexpressed in multiple myeloma (MM) [4]. Current therapies to target BCMA in MM include monoclonal antibodies, bi-specific antibodies and T cellular immunotherapies, CAR-T therapies [4, 5].

The human BCMA protein consists of 184 amino-acids: 1-54-extracellular domain; 55-77-transmembrane domain; 78-184-cytoplasmic domain. The amino-acid sequence of BCMA is shown on FIG. 2. BCMA lacks signaling peptide and resembles other receptors BAFF Receptor and transmembrane activator and cyclophilin ligand interactor and calcium modulator (TACI) [4]. These receptors play major role in B cell maturation and differentiation into plasma cells. Their ligands include BAFF and APRIL which expression is increase in MM patients [4].

BRIEF DESCRIPTION OF THE DRAWINGS

FIG. 5A shows CHO-BCMA target cells. on the right: From top to bottom: Mock CAR-T cells, T cells, target cells alone, and humanized CAR-T cells. FIG. 5B shows CHO target cells. From top to bottom on the right, Mock CAR-T cells, humanized BCMA CAR-T cells, T cells, and target cells alone.

DETAILED DESCRIPTION OF THE INVENTION

Definitions

Figures 1, 2:
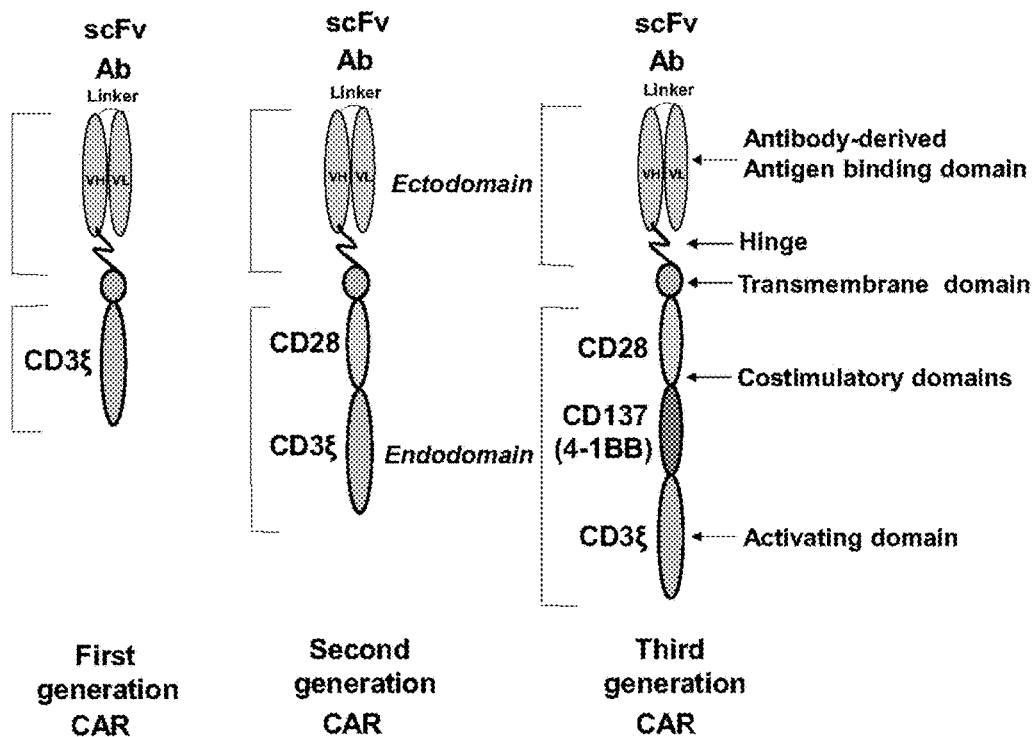
FIG. 1 shows the structures of CAR [3]. The left panel shows the structure of first generation (no costimulatory domains). The middle panel shows the structure of the second generation (one co-stimulation domain of CD28 or 4-BB). The right panel shows the structure of the third generation (two or more co-stimulation domains).
FIG. 2 shows the amino-acid sequence of BCMA protein (SEQ ID NO: 1). Extracellular domain is underlined.

As used herein, a "chimeric antigen receptor (CAR)" is a receptor protein that has been engineered to give T cells the new ability to target a specific protein. The receptor is chimeric because they combine both antigen-binding and T-cell activating functions into a single receptor. CAR is a fused protein comprising an extracellular domain capable of binding to an antigen, a transmembrane domain, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, a "domain" means one region in a polypeptide which is folded into a particular structure independently of other regions.

As used herein, "humanized antibodies" are antibodies derived from non-human species whose protein sequences have been modified to increase their similarity to antibody variants produced naturally in humans. For example, after a mouse antibody is developed, the DNA coding for that antibody can be sequenced. The DNA sequence corresponding to the antibody CDRs can then be determined. The CDR sequences can be inserted into a construct containing the DNA for a human antibody variant to prepare humanized antibodies.

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for engineering an scFv are known to a person skilled in the art.

As used herein, a "tumor antigen" means a biological molecule having antigenicity, expression of which causes cancer.

The inventors have engineered humanized BCMA scFv starting from heavy and light chain variable regions of mouse monoclonal antibody derived from a mouse monoclonal antibody, clone 4C8A. Mouse 4C8A antibody exhibits strong and selective binding to human BCMA [6]. The inventors have produced BCMA-CAR-T cells based on humanized BCMA antibody to target cancer cells overexpressing BCMA tumor antigen. The BCMA-CAR-T cells of the present invention have high cytotoxic activity against several cancer cell lines.

The present invention is directed to a humanized anti-human BCMA antibody comprising $V_H$ having the amino acid of SEQ ID NO: 3 and $V_L$ having the amino acid of SEQ ID NO: 5.

In one embodiment, the humanized anti-human BCMA antibody is a single-chain variable fragment (scFv). ScFv can be $V_H$-linker-$V_L$ or $V_L$-linker-$V_H$.

The present invention is also directed to a chimeric antigen receptor fusion protein comprising from N-terminus to C-terminus: (i) a single-chain variable fragment (scFv) against BCMA in which $V_H$ has the amino acid sequence of SEQ ID NO 3, and $V_L$ has the amino acid of SEQ ID NO: 5, (ii) a transmembrane domain, (iii) at least one co-stimulatory domains, and (iv) an activating domain.

In one embodiment, the CAR structure is shown in FIG. 2.

In one embodiment, the co-stimulatory domain is selected from the group consisting of CD28, 4-1BB, GITR, ICOS-1, CD27, OX-40 and DAP10. A preferred the co-stimulatory domain is CD28.

A preferred activating domain is CD3 zeta (CD3 Z or CD3ζ).

The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, a CD3 zeta chain, CD28, CD3ε, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. It is preferable that a triplet of phenylalanine, tryptophan and valine is found at each end of the synthetic transmembrane domain. Optionally, a short oligopeptide linker or a polypeptide linker, for example, a linker having a length of 2 to 10 amino acids can be arranged between the transmembrane domain and the intracellular domain. In one embodiment, a linker sequence having a glycine-serine continuous sequence can be used.

The present invention provides a nucleic acid encoding the BCMA-CAR. The nucleic acid encoding the CAR can be prepared from an amino acid sequence of the specified CAR by a conventional method. A base sequence encoding an amino acid sequence can be obtained from the aforementioned NCBI RefSeq IDs or accession numbers of GenBank for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

A nucleic acid encoding the CAR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. A virus vector lacking the replicating ability so as not to self-replicate in an infected cell is preferably used.

For example, when a retrovirus vector is used, a suitable packaging cell based on a LTR sequence and a packaging signal sequence possessed by the vector can be selected for preparing a retrovirus particle using the packaging cell. Examples of the packaging cell include PG13 (ATCC CRL-10686), PA317 (ATCC CRL-9078), GP+E-86 and GP+envAm-12, and Psi-Crip. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

A CAR-T cell binds to a specific antigen via the CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and a macrophage.

The cell expressing the CAR can be used as a therapeutic agent for a disease. The therapeutic agent comprises the cell expressing the CAR as an active ingredient, and it may further comprise a suitable excipient.

The inventors have generated CAR-T cells based on humanized BCMA ScFv sequence specifically targeting BCMA. The inventors have produced humanized BCMA-CAR-T cells to target cancer cells overexpressing BCMA tumor antigen. The humanized BCMA-CAR-T cells of the present invention secreted high level of cytokines against multiple myeloma cancer cells and kill CHO-BCMA-positive target cells but not control parental CHO cells.

The advantages of the humanized BCMA-ScFv of the present invention over the corresponding mouse ScFv include less immunogenicity to human due to the humanized BCMA scFv sequence. Thus, the humanized BCMA antibody of the present invention is highly potent and advantageous as therapeutic agents in many clinical applications.

The present humanized BCMA ScFv can be used for immunotherapy applications: toxin/drug-conjugated antibody, monoclonal therapeutic antibody, and CAR-T cell immunotherapy.

Humanized BCMA-CAR-T cells using the present humanized BCMA ScFv effectively target BCMA antigen in BCMA-positive cancer cell lines such as ovarian, colon, pancreatic, melanoma, cervical cancer, and other BCMA-positive cancers.

Humanized BCMA-CAR-T cells can be used in combination with different chemotherapy: checkpoint inhibitors, targeted therapies, small molecule inhibitors, and antibodies.

Humanized BCMA-CAR-T cells can be used clinically for BCMA-positive cancer cells.

Modifications of co-activation domains such as CD28, 4-1BB and others can be used to increase the efficacy of CAR-T cells. Tag-conjugated humanized BCMA scFv can be used for CAR generation.

Humanized BCMA-CAR-T cells can be used with different safety switches such as t-EGFR, RQR (Rituximab-CD34-Rituximab), inducible caspase-9 and other.

Third generation CAR-T or other co-activation signaling domains can be used with humanized BCMA-scFv to prepare BCMA-CAR-T.

The humanized BCMA CAR can be combined with CARs targeting other tumor antigens or tumor microenvironment, e.g., VEGFR-1-3, PDL-1. Bi-specific antibodies against BCMA and CD3, or other antigens can be generated for therapy.

The humanized BCMA-CAR can be used for generating other types of cells such as CAR-natural killer (NK) cells, BCMA-CAR-macrophages, allogenic CAR-T cells, gene-edited T cells, and other BCMA-CAR hematopoietic cells, which can target BCMA-positive cancers.

The present invention provides T cells, NK cells, macrophages, or hematopoietic cells, modified to express BCMA-CAR.

BCMA-CAR-T cells can be used against cancer stem cells and circulating tumor stem cells that are most resistant against chemotherapy and form aggressive tumors.

BCMA-CAR-T cells, BCMA-NK cells, BCMA-macrophages, and other cells can be used for targeting different types of cancers.

BCMA-CAR-T cells can be delivered intra-tumorally to patients for increased safety.

The following examples further illustrate the present invention. These examples are intended merely to be illustrative of the present invention and are not to be construed as being limiting.

EXAMPLES

Example 1

Humanized BCMA VH and VL and scFv Sequences

The BCMA scFv was derived from hybridoma clones 4C8A (WO2019/195017). The sequences of heavy and light chain variable regions of mouse clone 4C8A were determined and used to construct a humanized scFv.

The structure of humanized BCMA (PMC306) scFv is: $V_H$-linker-$V_L$. Linker is G4Sx3.

The bold highlights the nucleotide sequence of humanized BCMA PMC306 ScFv clone: $V_H$; the underlined highlights the nucleotide sequence of $V_L$; in between (italicized) is the nucleotide sequence encoding a linker.

(SEQ ID NO: 2)
caggtgcagctggtgcagagcggcgcggaagtgaaaaaaccgggcagcag cgtgaaagtgagctgcaaagcgagcggctataccttaccagctatgtga tgcattgggtgcgccaggcgccgggccagggcctggaatggatgggctat attattccgtataacgatgcgaccaaatataacgaaaaatttaaaggccg cgtgaccattaccgcggataaaagcaccagcaccgcgtatatggaactga gcagcctgcgcagcgaagataccgcggtgtattattgcgcgcgctataac tatgatggctattttgatgtgtggggccagggcaccctggtgaccgtgag cagc*ggcggcggcggcagcggcggcggcggcagcggcggcggcggcagcg*

*aaattgtgctgacccagagcccggcgaccctgagcctgagcccgggcgaa*

*cgcgcgacccttgagctgccgcgcgagccagagcattagcgattatctgca*

*ttggtatcagcagaaaccgggccaggcgccgcgcctgctgatttattatg*

*cgagccagagcattaccggcattccggcgcgctttagcggcagcggcagc*

*ggcaccgatttacctgaccattagcagcctggaaccggaagattttgc*

*ggtgtattattgccagaacggccatagctttccgccgacctttggcggcg*

*gcaccaaagtggaaattaaa*

PMC306 V_H amino acid sequence:
(SEQ ID NO: 3)
QVQLVQSGAEVKKPGSSVKVSCKASGYTFTSYVMHWVRQAPGQGLEWMGY

IIPYNDATKYNEKFKGRVTITADKSTSTAYMELSSLRSEDTAVYYCARYN

YDGYFDVWGQGTLVTVSS

Linker amino acid sequence
(SEQ ID NO: 4)
GGGGSGGGGSGGGGS

PCM306 V_L amino acid sequence:
(SEQ ID NO: 5)
EIVLTQSPATLSLSPGERATLSCRASQSISDYLHWYQQKPGQAPRLLIYY

ASQSITGIPARFSGSGSGTDFTLTISSLEPEDFAVYYCQNGHSFPPTFGG

GTKVEIK

Humanized BCMA (PMC306) scFv Protein:
(SEQ ID NO: 6)
Q V Q L V Q S G A E V K K P G S S V K V S C K A S

G Y T F T S Y V M H W V R Q A P G Q G L E W M G Y

I I P Y N D A T K Y N E K F K G R V T I T A D K S

T S T A Y M E L S S L R S E D T A V Y Y C A R Y N

Y D G Y F D V W G Q G T L V T V S S G G G G S G G

G G S G G G G S E I V L T Q S P A T L S L S P G E

R A T L S C R A S Q S I S D Y L H W Y Q Q K P G Q

A P R L L I Y Y A S Q S I T G I P A R F S G S G S

G T D F T L T I S S L E P E D F A V Y Y C Q N G H

S F P P T F G G G T K V E I K

Example 2

Humanized BCMA-CAR Sequences

Figure 3:
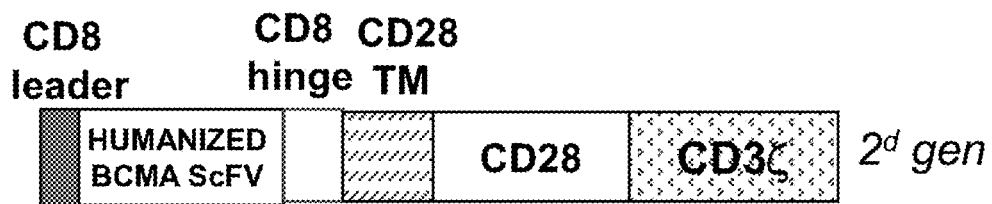
FIG. 3 shows the structure of humanized BCMA CAR construct.

The scheme of humanized (PMC306) BCMA-CAR construct is shown on FIG. 3. Lentiviral vector with EF1a promoter was used for cloning of humanized scFv CAR sequences.

The BCMA-CAR structure includes human CD8 signaling peptide, humanized BCMA scFv (V_H-Linker-V_L), CD8 hinge, CD28 transmembrane, activation domains CD3 zeta (FIG. 3).

The nucleotide sequences and some of the amino acid sequences of CD8 signaling-BCMA scFv (V_H-Linker-V_L)-CD8 hinge-CD28 TM-CD28-CD3-zeta are shown below.

<CD8 leader>
Nucleotide
(SEQ ID NO: 7)
ATGGCCTTACCAGTGACCGCCTTGCTCCTGCCGCTGGCCTTGCTGCTCCA

CGCCGCCAGGCCG

Amino Acid
(SEQ ID NO: 8)
MALPVTALLLPLALLLHAARP

<Nhe I site>
gctagc

<Humanized BCMA, PMC 306 scFv>

VH-linker-VL, see Example 1 for nucleic acid sequences and amino acid sequences.

<XhoI restriction site>
CTCGAG

<CD8 hinge>
Nucleotide
(SEQ ID NO: 9)
AAGCCCACCACGACGCCAGCGCCGCGACCACCAACACCGGCGCCCACCAT

CGCGTCGCAGCCCCTGTCCCTGCGCCCAGAGGCGAGCCGGCCAGCGGCGG

GGGGCGCAGTGCACACGAGGGGGCTGGACTTCGCCAGTGAT

Amino Acid
(SEQ ID NO: 10)
KPTTTPAPRPPTPAPTIASQPLSLRPEASRPAAGGAVHTRGLDFASD

<aagccc>

<CD28 transmembrane>
Nucleotide
(SEQ ID NO: 11)
TTTTGGGTGCTGGTGGTGGTTGGTGGAGTCCTGGCTTGCTATAGCTTGCT

AGTAACAGTGGCCTTTATTATTTTCTGGGTG

Amino Acid
(SEQ ID NO: 12)
FWVLVVVGGVLACYSLLVTVAFIIFWV

<CD28 co-stimulatory>
Nucleotide
(SEQ ID NO: 13)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC

Amino acid
(SEQ ID NO: 14)
RSKRSRLLHSDYMNMTPRRPGPTRKHYQPYAPPRDFAAYRS

<CD3 zeta> stop codons underlined
Nucleotide
(SEQ ID NO: 15)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGCAG

AGAAGGAAGAACCCTCAGGAAGGCCTGTACAATGAACTGCAGAAAGATAA

GATGGCGGAGGCCTACAGTGAGATTGGGATGAAAGGCGAGCGCCGGAGGG

GCAAGGGGCACGATGGCCTTTACCAGGGTCTCAGTACAGCCACCAAGGAC

ACCTACGACGCCCTTCACATGCAGGCCCTGCCCCCTCGCTAAtag

Amino acid
(SEQ ID NO: 16)
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR

-continued

<EcoRI restriction site>
gaattc

Translated amino-acid sequence of humanized
BCMA-CAR protein (SEQ ID NO: 17)
(SEQ ID NO: 17)

M A L P V T A L L L P L A L L L H A A R P A S Q V

Q L V Q S G A E V K K P G S S V K V S C K A S G Y

T F T S Y V M H W V R Q A P G Q G L E W M G Y I I

P Y N D A T K Y N E K F K G R V T I T A D K S T S

T A Y M E L S S L R S E D T A V Y Y C A R Y N Y D

G Y F D V W G Q G T L V T V S S G G G G S G G G G

S G G G G S E I V L T Q S P A T L S L S P G E R A

T L S C R A S Q S I S D Y L H W Y Q Q K P G Q A P

R L L I Y Y A S Q S I T G I P A R F S G S G S G T

D F T L T I S S L E P E D F A V Y Y C Q N G H S F

P P T F G G G T K V E I K L E K P T T T P A P R P

P T P A P T I A S Q P L S L R P E A S R P A A G G

A V H T R G L D F A S D K P F W V L V V V G G V L

A C Y S L L V T V A F I I F W V R S K R S R L L H

S D Y M N M T P R R P G P T R K H Y Q P Y A P P R

D F A A Y R S R V K F S R S A D A P A Y Q Q G Q N

Q L Y N E L N L G R R E E Y D V L D K R R G R D P

E M G G K P Q R R K N P Q E G L Y N E L Q K D K M

A E A Y S E I G M K G E R R R G K G H D G L Y Q G

L S T A T K D T Y D A L H M Q A L P P R

Example 3

CAR lentivirus Production

Lentivirus was produced by the standard procedure using 293T cells as described in [7] The inventors generated humanized BCMA-ScFv-CAR constructs inside lentiviral vector cloned into Xba I and Eco R I sites of lentiviral vector. pCD510-FMC63-28z lentiviral CAR construct containing the humanized BCMA ScFv-CD28-CD3zeta insert—between the Xba I and Eco RI cloning sites.

The lentiviruses were generated in 293T cells and the titers were established by RT-PCR. Then equal dose of lentiviruses was used for transduction of T cells.

Example 4

Peripheral Blood Mononuclear Cell (PBMC)
Isolation from Whole Blood

Whole blood (Stanford Hospital Blood Center, Stanford, Calif.) was collected from individual or mixed donors (depending on the amount of blood required) in 10 mL Heparin vacutainers (Becton Dickinson). Approximately 10 ml of whole anti-coagulated blood was mixed with sterile phosphate buffered saline (PBS) buffer for a total volume of 20 ml in a 50 ml centrifuge tube (PBS, pH 7.4, without Ca+2 and Mg+2). The blood/PBS (20 ml) was layered on top of 15 mL of Ficoll-Paque PLUS (GE Healthcare) in a conical centrifuge tube gently, and the sample was centrifuged at 400×g for 30-40 min at room temperature. The layer of cells containing peripheral blood mononuclear cells (PBMC) at the diluted plasma/Ficoll interface was removed, washed, and centrifuged at 200×g for 10 min at room temperature. Cells were counted with a hemocytomter. The PBMC were washed once with CAR-T media (AIM V-AlbuMAX(BSA) (Life Technologies), with 5% AB serum and 1.25 µg/mL amphotericin B (Gemini Bioproducts, Woodland, Calif.), 100 U/mL penicillin, and 100 µg/mL streptomycin) and used for experiments or were frozen at −80° C.

Example 5

T-Cell Activation from PBMC

The isolated PBMC cells are resuspended in CAR-T medium with 300 U/mL huIL2 (from a 1000× stock; Invitrogen) and mixed with CD3-CD28 beads at a 1:1 bead-to-cell ratio. The cells are incubated at 37° C. in the presence of CO2 for 24 hours before viral transduction.

Example 6

T-Cell Transduction and Expansion

Following activation of PBMC, cells were incubated for 24 hours at 37° C., 5% $CO_2$. To each well of 1×10$^6$ cells, 5×10$^6$ lentivirus and 2 µL/mL of media of Transplus (Alstem, Richmond, Calif.) (a final dilution of 1:500) were added. Cells were incubated for an additional 24 hours before repeating the addition of virus. Cells were then grown in the continued presence of 300 U/ML of IL-2 fresh medium with IL-2 for a period of 12-14 days (total incubation time was dependent on the final umber of CAR-T cells required). Cells concentrations were analyzed every 2-3 days, with media being added at that time to dilute the cell suspension to 1×10$^6$ cells/mL.

Example 7

Humanized BCMA-CAR-T Cells Expressed BCMA scFv

Figure 4:
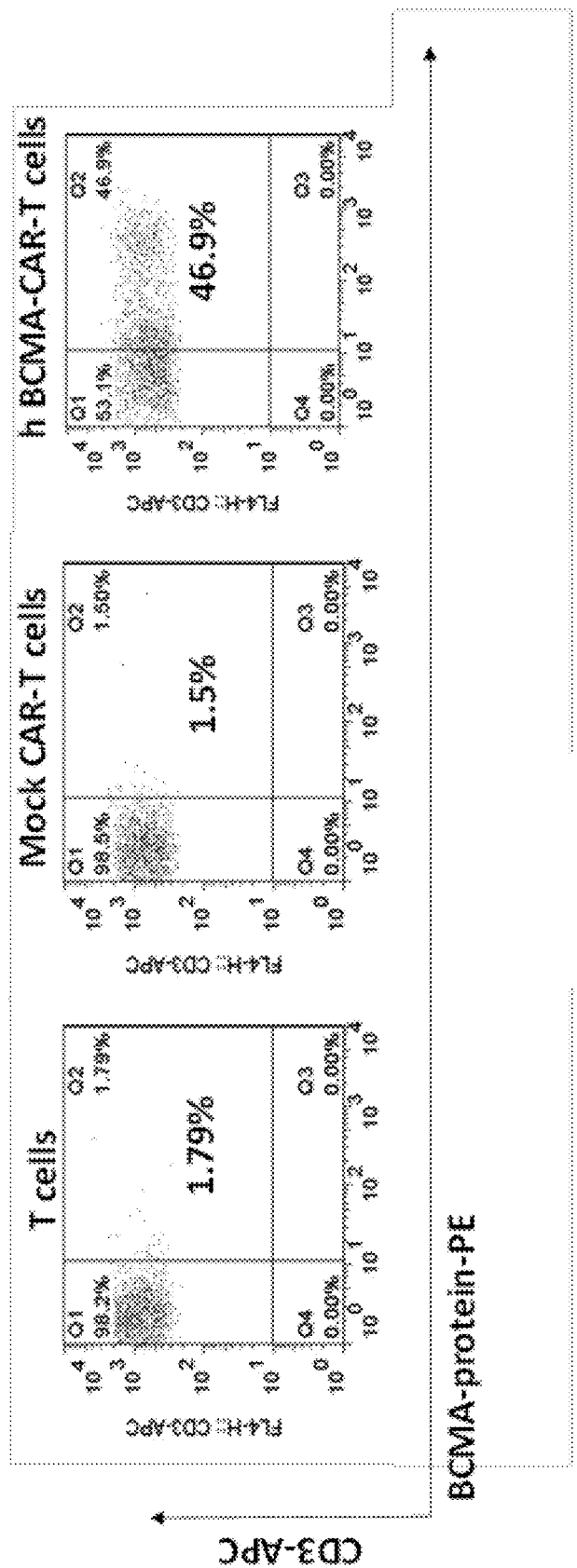
FIG. 4 shows that humanized BCMA-CAR construct was detected by FACS analysis with fluorescently labeled recombinant BCMA protein. Humanized BCMA-CAR-positive cells were detected after transduction of lentiviral humanized BCMA-CAR into T cells.

We designed humanized BCMA-CAR-T cells with humanized BCMA-CAR construct shown in Example 2. We used Mock scFv with unrelated ScFv and generated Mock-CAR-T cells as a negative control. Humanized BCMA-CAR-positive cells were detected after transduction of lentiviral humanized BCMA CAR into T cells. (FIG. 4).

Example 8

Humanized BCMA-CAR-T Cells Killed
CHO-BCMA Cells But Not CHO Cells

Figure 5A:
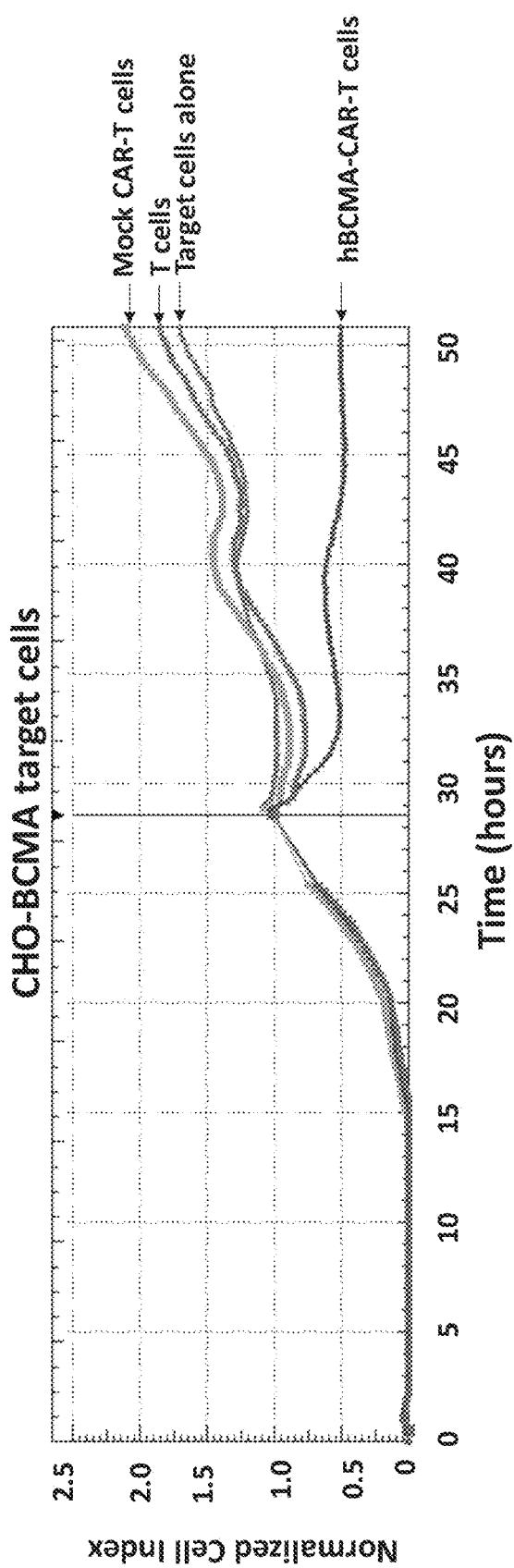
FIGS. 5A-5B show that humanized BCMA-CAR-T cells killed CHO-BCMA cells but not CHO cells. XCelligence Real-time cytotoxicity assay was used for detection of humanized BCMA-CAR-T cell cytotoxicity. Normalized cell index is shown on Y-axis, and time is shown on X-axis.
Figure 5B:
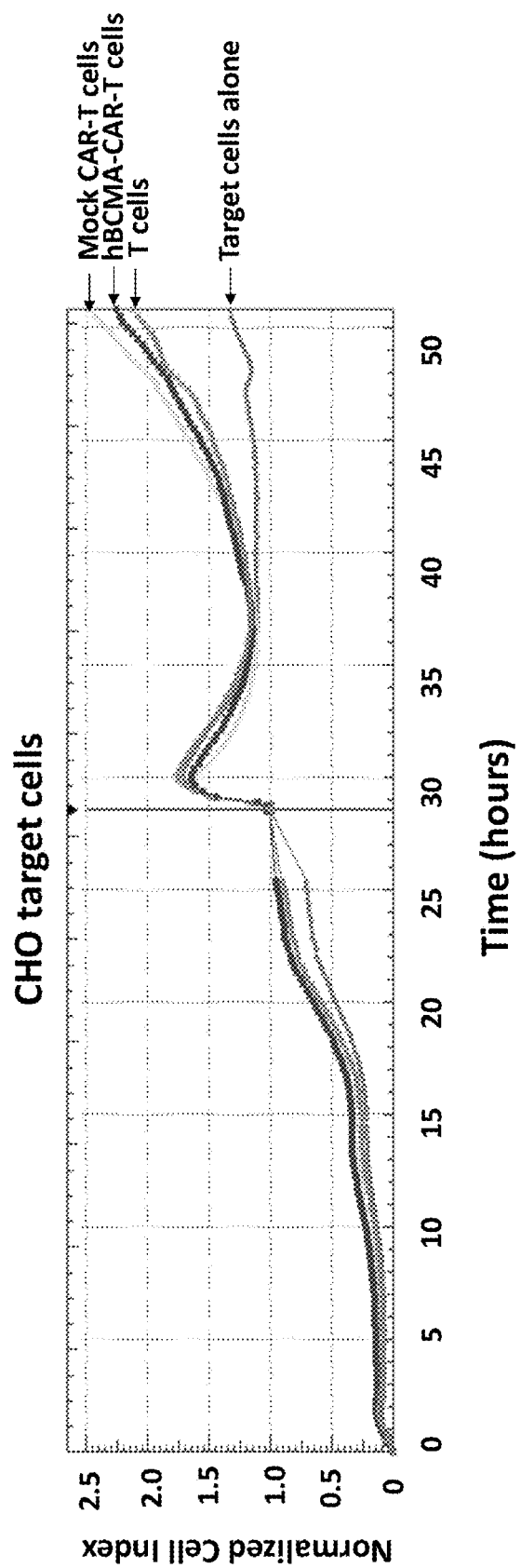

We incubated humanized BCMA-CAR-T cells with target CHO-BCMA target cells and CHO (BCMA-negative) control cells. Humanized BCMA-CAR-T cells specifically killed CHO-BCMA cells (FIG. 5A) but not CHO cells (FIG. 5B). The results demonstrate high specificity of humanized BCMA-CAR-T cells to target BCMA antigen and to kill BCMA-positive cells.

Example 9

Figure 6:
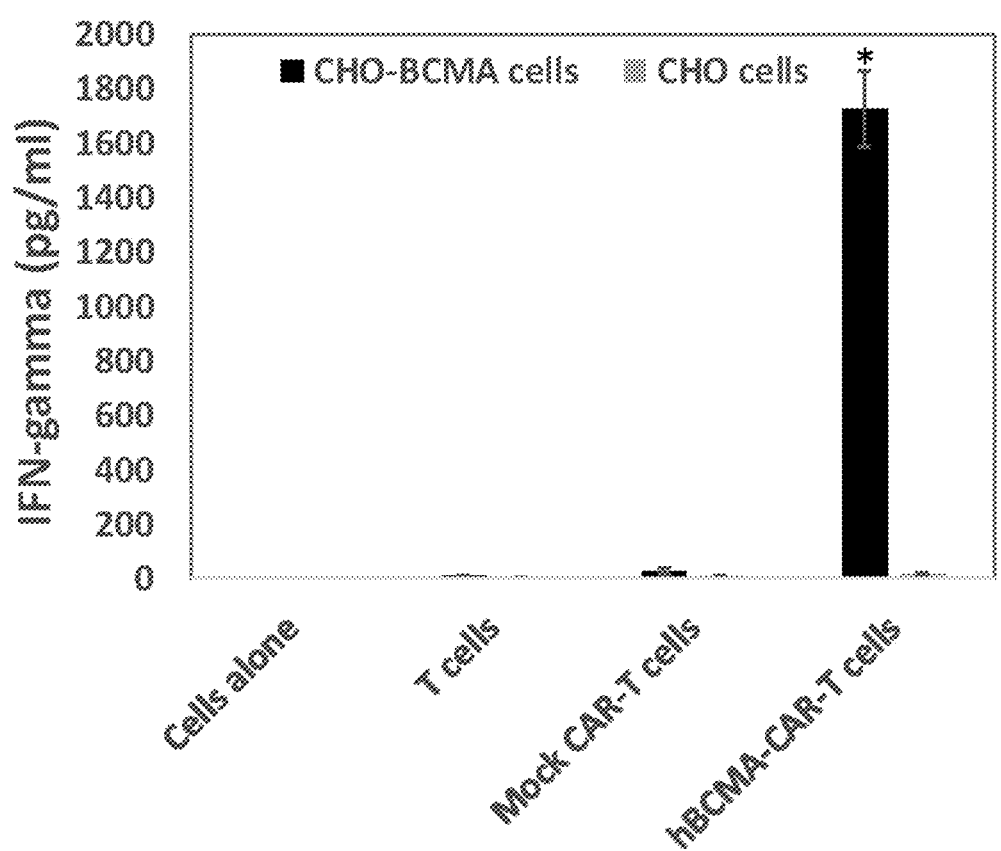
FIG. 6 shows that humanized BCMA-CAR-T cells, secreted high level of IFN-gamma with CHO-BCMA-positive cells, but not with BCMA-negative CHO control cells. $p<0.05$ IFN-gamma secretion in CHO-BCMA cells of BCMA-CAR-T cells versus T cells and Mock CAR-T cells.

Humanized CAR-T Cells Secreted IFN-gamma Against Target CHO-BCMA Cells Significantly But Not Against CHO Cells We collected supernatant after co-incubation of humanized BCMA-CAR-T cells and target CHO-BCMA and parental CHO cells and performed IFN-gamma assay. BCMA-CAR-T cells secreted IFN-gamma with CHO-BCMA cells but not with negative control CHO cells (FIG. 6). The results confirm specificity of humanized BCMA-CAR-T cells.

Example 10

Figure 7:
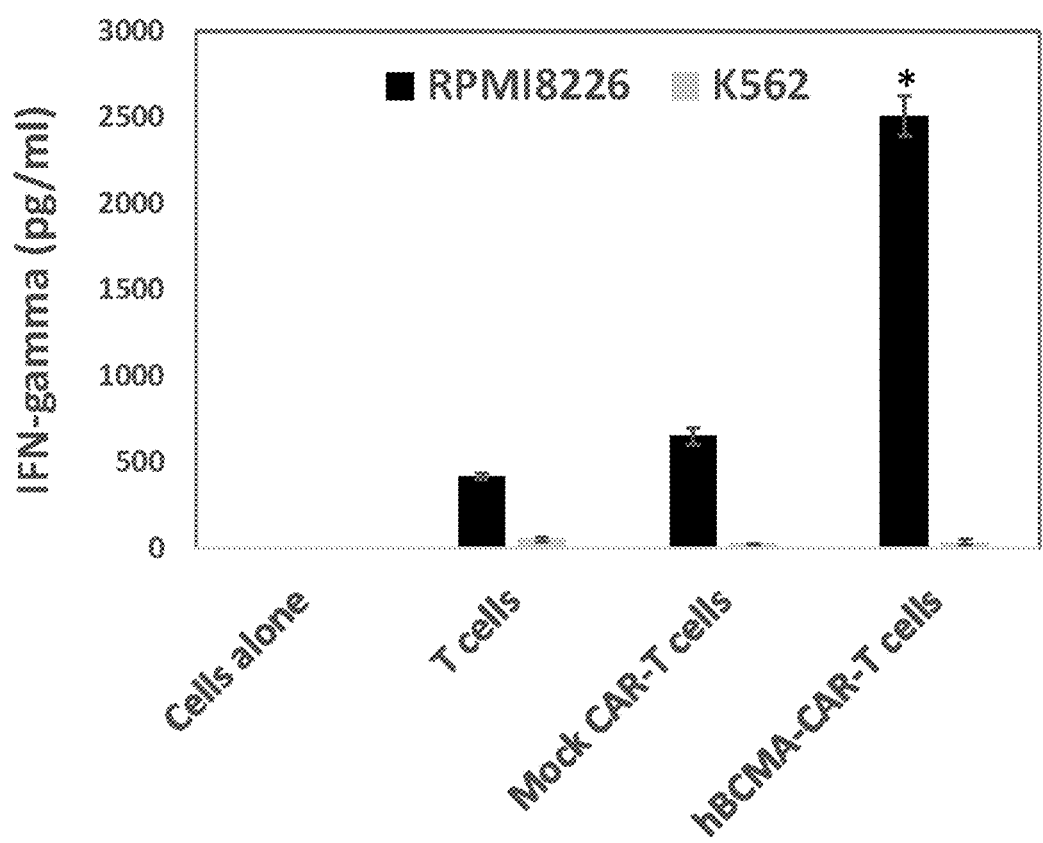
FIG. 7 shows humanized BCMA-CAR-T cells secreted high level of IFN-gamma against multiple myeloma cells but not against BCMA-negative K562 control cells. *$p<0.05$, IFN-gamma secretion in multiple myeloma cells of BCMA-CAR-T cells versus T cells and Mock-CAR-T cells.

Humanized CAR-T Cells Secreted High Levels of IFN-gamma Against BCMA-positive RPMI8226 Multiple Myeloma Cells But Not Against BCMA-negative K562 Leukemia Cells We incubated BCMA-CAR-T cells with multiple myeloma cancer cells RPMI8266, and BCMA-negative K562 cells (chronic myelogenous leukemia cells) and performed ELISA with IFN-gamma using kit from Fisher, according to manufacturer's protocol. Humanized BCMA-CAR-T cells secreted high level of IFN-gamma against BCMA-positive multiple myeloma cancer cells but not against BCMA-negative K562 cells (FIG. 7). The level of killing and secretion of IFN-gamma was significantly higher with BCMA-CAR-T cells than with T cells and Mock CAR-T cells. This confirms specificity of humanized BCMA-CAR-T cells against hematological BCMA-positive cells.

Example 11

Figure 8A:
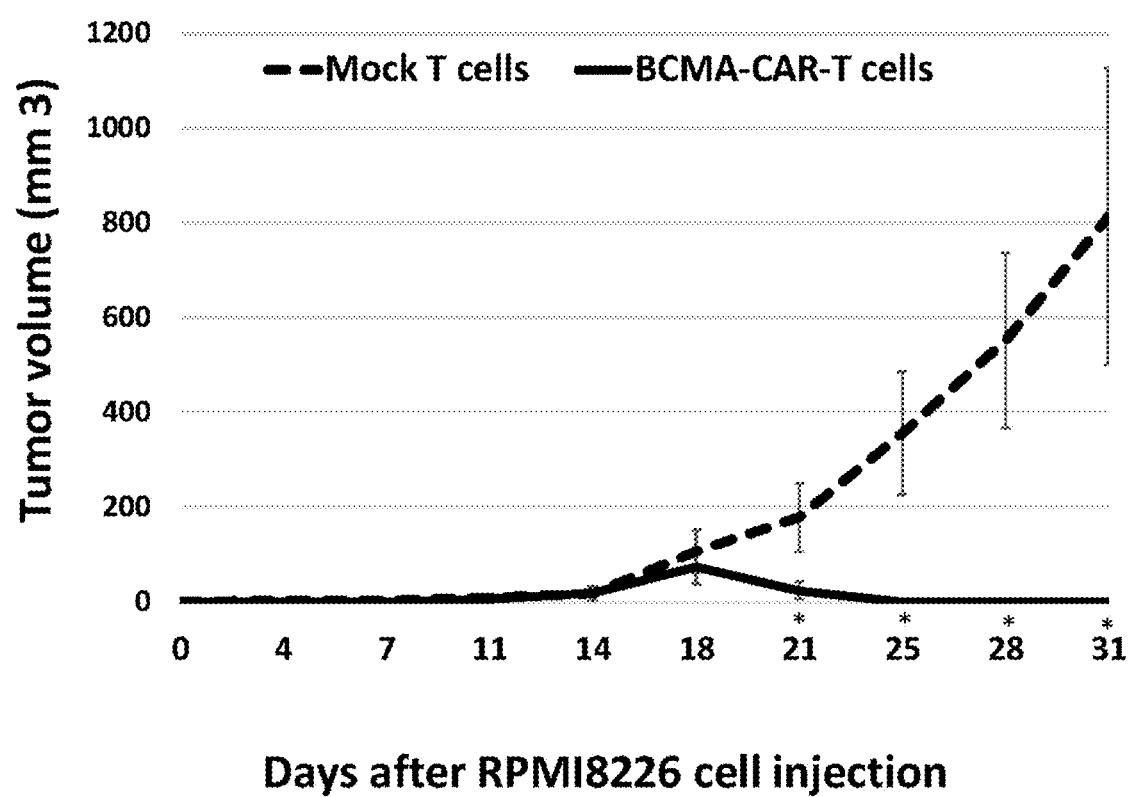
FIG. 8A shows humanized BCMA-CAR-T cells significantly decreased RPMI8226 xenograft tumor growth. CAR-T cells were injected at day 7 and 20 by i.v $1\times10^7$ cells/mice. Bars show average tumor volume+/−standard errors. *$p<0.05$, BCMA CAR-T cells vs Mock T cells.
Figure 8B:
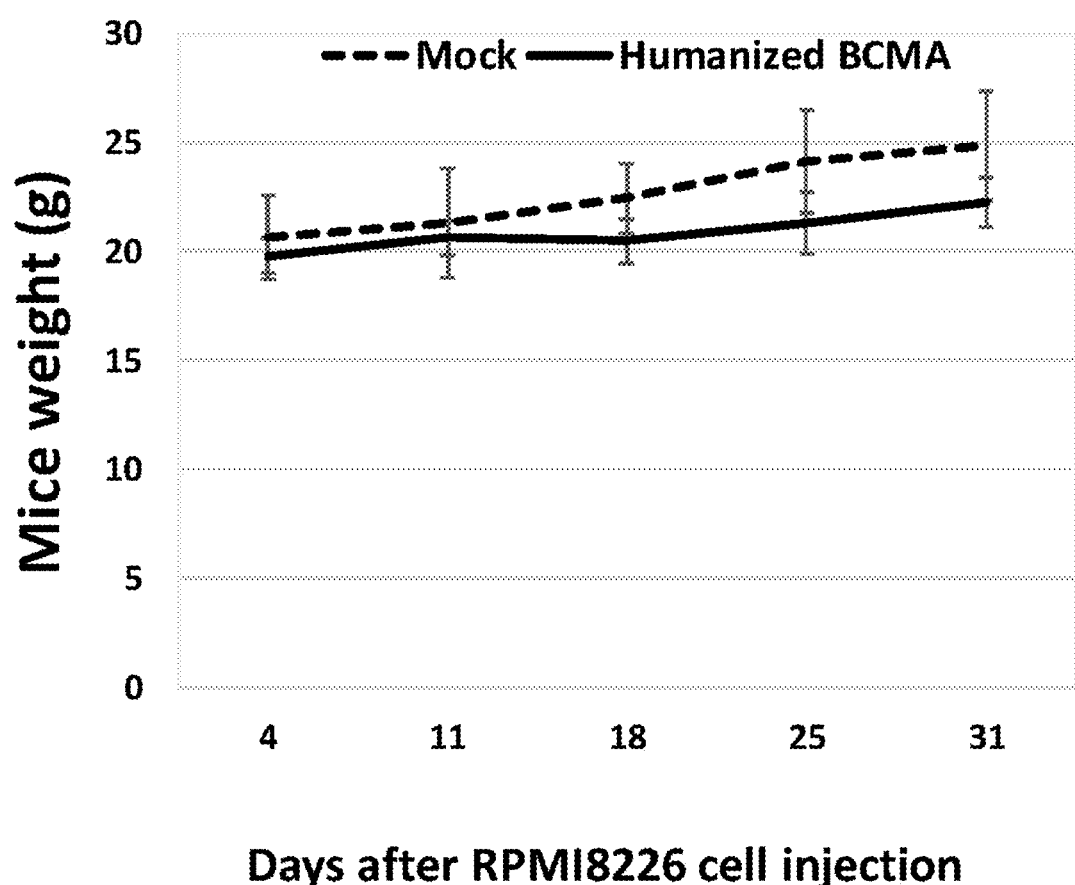
FIG. 8B shows that humanized BCMA-CAR-T cells did not decrease mouse body weight. Bars show average mice body weight+/−standard deviations.

Humanized BCMA-CAR-T Cells Significantly Decreased RPMI8226 Xenograft Tumor Growth in Mouse Model In Vivo Multiple myeloma RPMI8226 cells were injected subcutaneously into NSG mice (1×10^7 cells/mice), and then humanized BCMA-CAR-T cells were injected twice by i.v. (1×10^7 CAR-T cells/mice). Humanized BCMA-CAR-T cells significantly decreased RPMI8226 tumor growth in mice (FIG. 8A). Mice treated with humanized BCMA-CAR-T cells did not cause decreased mice body weight suggesting that CAR-T cells were not toxic to mice (FIG. 8B). No behavior or visual changes were observed during the study.

Figure 8C:
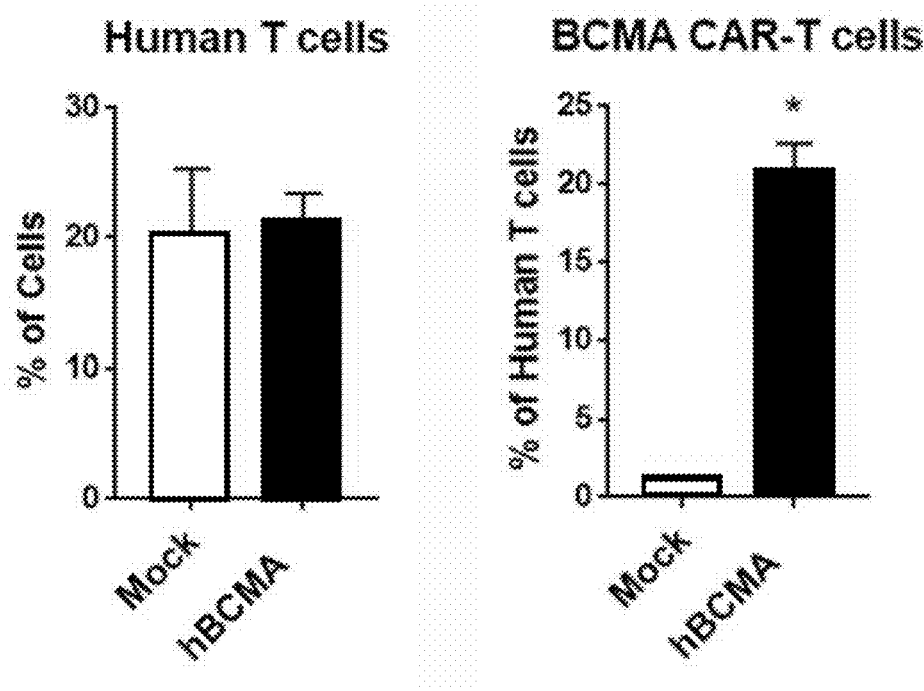
FIG. 8C shows that humanized BCMA-CAR-T cells, but not Mock-Car-T-cells, were detected in the mouse blood by FACS with BCMA recombinant protein. The peripheral blood cells were analyzed by flow cytometry at the end of the study for binding to human BCMA protein and antibodies specific for human T (CD4+/CD8+) cells. The percentage of cells binding to the CD4 antibody is shown on the left panel of FIG. 8C, and the percentage of those human T cells that also bound to the BCMA protein is shown on the right panel of FIG. 8C.

The peripheral blood cells were analyzed by flow cytometry at the end of the study for binding to human BCMA protein and antibodies specific for human T (CD4+/CD8+) cells. The percentage of cells binding to the CD4 mAb is shown on the left panel of FIG. 8C, and the percentage of those human T cells that also bound to the BCMA protein is shown on the right panel of FIG. 8C. The results show that humanized BCMA-CAR-T cells, but not Mock-Car-T-cells, were detected in the mouse blood by FACS with BCMA recombinant protein.

REFERENCES

1. Maus, M. V., Haas, A. R., Beatty, G. L., Albelda, S. M., Levine, B. L., Liu, X., Zhao, Y., Kalos, M., and June, C. H. (2013). T cells expressing chimeric antigen receptors can cause anaphylaxis in humans. Cancer Immunol Res 1, 26-31.
2. Maus, M. V., Grupp, S. A., Porter, D. L., and June, C. H. (2014). Antibody-modified T cells: CARs take the front seat for hematologic malignancies. Blood 123, 2625-2635.
3. Golubovskaya V, Wu L. (2016) Different Subsets of T Cells, Memory, Effector Functions, and CAR-T Immunotherapy. Cancers, 15, 8 (3). PMID: 26999211
4. Ali, S. A., Shi, V., Maric, I., Wang, M., Stroncek, D. F., Rose, J. J., Brudno, J. N., Stetler-Stevenson, M., Feldman, S. A., Hansen, B. G., et al. (2016). T cells expressing an anti-B-cell maturation antigen chimeric antigen receptor cause remissions of multiple myeloma. Blood 128, 1688-1700.
5. Tai, Y. T., and Anderson, K. C. (2015). Targeting B-cell maturation antigen in multiple myeloma. Immunotherapy. 7(11):1187-99. doi: 10.2217/imt.15.77. Epub 2015 Sep. 15. Review. PMID: 26370838
6. WO2019/195017
7. Berahovich R, Xu S, Zhou H, Harto H, Xu Q, Garcia A, Liu F, Golubovskaya V M, Wu L. FLAG-tagged CD19-specific CAR-T cells eliminate CD19-bearing solid tumor cells in vitro and in vivo. Front Biosci (Landmark Ed). 2017 Jun. 1; 22: 1644-1654

---

What is claimed is:

1. An anti-BCMA single-chain variable fragment (scFv), comprising:
   a heavy chain variable region ($V_H$) comprising the amino acid sequence of SEQ ID NO: 3; and
   a light chain variable region $V_L$) comprising the amino acid sequence of SEQ ID NO: 5.

2. The scFv of claim 1, further comprising a linker in between the $V_H$ and the $V_L$.

3. The scFv of claim 2, wherein the linker comprises SEQ ID NO: 4.

4. The scFv of claim 2, comprising the amino acid sequence of SEQ ID NO: 14.

5. An anti-BCMA chimeric antigen receptor (CAR), comprising:
   an anti-BCMA single-chain variable fragment (scFv) comprising
      a heavy chain variable region ($V_H$) comprising the amino acid sequence of SEQ ID NO: 3, and
      a light chain variable region $V_L$) comprising the amino acid sequence of SEQ ID NO: 5;
   a transmembrane domain;
   a co-stimulatory domain; and
   an activating domain.

6. The CAR of claim 5, wherein the transmembrane domain is a transmembrane domain selected from the group consisting of a T cell receptor α chain, a T cell receptor β chain, a CD3 zeta chain, a CD28, a CD3ε, a CD45, a CD4, a CD5, a CD8, a CD9, a CD16, a CD22, a CD33, a CD37, a CD64, a CD80, a CD86, a CD134, a CD137, an ICOS, a CD154, and a GITR.

7. The CAR of claim 6, wherein the transmembrane domain comprises a transmembrane domain of a CD8.

8. The CAR of claim 5, wherein the co-stimulatory domain is a co-stimulatory domain selected from the group consisting of a CD28, a 4-1BB, a GITR, an ICOS-1, a CD27, an OX-40, and a DAP10.

9. The CAR of claim 8, wherein the co-stimulatory domain comprises a 4-1BB co-stimulatory domain.

10. The CAR of claim 5, wherein the activating domain comprises a CD3 zeta activating domain.

11. The CAR of claim 5, wherein the transmembrane domain comprises a transmembrane domain of a CD8, the co-stimulatory domain comprises a 4-1BB co-stimulatory domain, and the activating domain comprises a CD3 zeta activating domain.

12. The CAR of claim 5, comprising the amino acid sequence of SEQ ID NO: 17.

13. A CAR-T cell, comprising the CAR of claim 5.

14. A CAR-T cell, comprising the CAR of claim 12.

15. A method of killing BCMA-overexpressing multiple myeloma cancer cells comprising: contacting the BCMA-overexpressing multiple myeloma cancer cells with a CAR-T cell comprising
  an anti-BCMA single-chain variable fragment (scFv) comprising
    a heavy chain variable region ($V_H$) comprising the amino acid sequence of SEQ ID NO: 3, and
    a light chain variable region $V_L$) comprising the amino acid sequence of SEQ ID NO: 5;
  a transmembrane domain;
  a co-stimulatory domain; and
  an activating domain.

16. The method of claim 15, wherein the contacting is in vitro.

17. The method of claim 15, wherein the multiple myeloma cancer cells comprise human cells.

18. The method of claim 15, wherein the contacting is intra-tumoral.

* * * * *

UNITED STATES PATENT AND TRADEMARK OFFICE
CERTIFICATE OF CORRECTION

PATENT NO. : 10,927,182 B2
APPLICATION NO. : 17/010798
DATED : February 23, 2021
INVENTOR(S) : Lijun Wu and Vita Golubovskaya Page 1 of 1

It is certified that error appears in the above-identified patent and that said Letters Patent is hereby corrected as shown below:

In the Claims

In Claim 1, Column 23, Line 54, delete "region V" and insert --region (V--

In Claim 5, Column 24, Line 49, delete "region V" and insert --region (V--

In Claim 15, Column 25, Line 20, delete "region V" and insert --region (V--

In Claim 15, Column 25, Lines 12-15, delete
"A method of killing BCMA-overexpressing multiple
myeloma cancer cells comprising: contacting the BCMA-
overexpressing multiple myeloma cancer cells with a
CAR-T cell comprising" and insert
--A method of killing BCMA-overexpressing multiple myeloma cancer cells comprising:
    contacting the BCMA-overexpressing multiple myeloma cancer cells with a CAR-T cell comprising--

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 17

<210> SEQ ID NO 1
<211> LENGTH: 184
<212> TYPE: PRT
<213> ORGANISM: Homo sapiens

<400> SEQUENCE: 1

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60
```

```
Ile Ile Ser Leu Ala Val Phe Val Leu Met Phe Leu Leu Arg Lys Ile
 65                  70                  75                  80

Asn Ser Glu Pro Leu Lys Asp Glu Phe Lys Asn Thr Gly Ser Gly Leu
                 85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
                115                 120                 125

Glu Asp Cys Ile Lys Ser Lys Pro Lys Val Asp Ser Asp His Cys Phe
        130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 2
<211> LENGTH: 720
<212> TYPE: DNA
<213> ORGANISM: Homo sapiens

<400> SEQUENCE: 2
caggtgcagc tggtgcagag cggcgcggaa gtgaaaaaac cgggcagcag cgtgaaagtg      60
agctgcaaag cgagcggcta cctttacc agctatgtga tgcattgggt gcgccaggcg       120
ccgggccagg gcctggaatg gatgggctat attattccgt ataacgatgc gaccaaatat     180
aacgaaaaat ttaaaggccg cgtgaccatt accgcggata aaagcaccag caccgcgtat     240
atggaactga gcagcctgcg cagcgaagat accgcggtgt attattgcgc gcgctataac    300
tatgatggct attttgatgt gtggggccag ggcacccctgg tgaccgtgag cagcggcggc    360
ggcggcagcg gcggcggcgg cagcggcggc ggcggcagcg aaattgtgct gacccagagc    420
ccggcgaccc tgagcctgag cccgggcgaa cgcgcgaccc tgagctgccg cgcgagccag    480
agcattagcg attatctgca ttggtatcag cagaaaccgg gccaggcgcc gcgcctgctg    540
atttattatg cgagccagag cattaccggc attccggcgc gctttagcgg cagcggcagc    600
ggcaccgatt ttaccctgac cattagcagc ctggaaccgg aagattttgc ggtgtattat    660
tgccagaacg ccatagcctt ccgccgacc tttggcggcg gcaccaaagt ggaaattaaa    720

<210> SEQ ID NO 3
<211> LENGTH: 118
<212> TYPE: PRT
<213> ORGANISM: Homo sapiens

<400> SEQUENCE: 3

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Thr Phe Thr Ser Tyr
             20                  25                  30

Val Met His Trp Val Arg Gln Ala Pro Gly Gln Gly Leu Glu Trp Met
         35                  40                  45

Gly Tyr Ile Ile Pro Tyr Asn Asp Ala Thr Lys Tyr Asn Glu Lys Phe
     50                  55                  60

Lys Gly Arg Val Thr Ile Thr Ala Asp Lys Ser Thr Ser Thr Ala Tyr
 65                  70                  75                  80
```

```
Met Glu Leu Ser Ser Leu Arg Ser Glu Asp Thr Ala Val Tyr Tyr Cys
                85                  90                  95

Ala Arg Tyr Asn Tyr Asp Gly Tyr Phe Asp Val Trp Gly Gln Gly Thr
            100                 105                 110

Leu Val Thr Val Ser Ser
        115

<210> SEQ ID NO 4
<211> LENGTH: 15
<212> TYPE: PRT
<213> ORGANISM: Artificial Sequence
<220> FEATURE:
<223> OTHER INFORMATION: synthetic

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 107
<212> TYPE: PRT
<213> ORGANISM: Homo sapiens

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp Tyr
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Pro
                85                  90                  95

Thr Phe Gly Gly Gly Thr Lys Val Glu Ile Lys
            100                 105

<210> SEQ ID NO 6
<211> LENGTH: 240
<212> TYPE: PRT
<213> ORGANISM: Homo sapiens

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
        35                  40                  45

Gly Tyr Ile Ile Pro Tyr Asn Asp Ala Thr Lys Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asn Tyr Asp Gly Tyr Phe Asp Val Trp Gly Gln Gly Thr
```

```
                    100                 105                 110
Leu Val Thr Val Ser Ser Gly Gly Gly Gly Gly Gly Gly Gly Ser
            115                 120                 125
Gly Gly Gly Gly Ser Glu Ile Val Leu Thr Gln Ser Pro Ala Thr Leu
            130                 135                 140
Ser Leu Ser Pro Gly Glu Arg Ala Thr Leu Ser Cys Arg Ala Ser Gln
145                 150                 155                 160
Ser Ile Ser Asp Tyr Leu His Trp Tyr Gln Gln Lys Pro Gly Gln Ala
                165                 170                 175
Pro Arg Leu Leu Ile Tyr Tyr Ala Ser Gln Ser Ile Thr Gly Ile Pro
            180                 185                 190
Ala Arg Phe Ser Gly Ser Gly Ser Gly Thr Asp Phe Thr Leu Thr Ile
            195                 200                 205
Ser Ser Leu Glu Pro Glu Asp Phe Ala Val Tyr Tyr Cys Gln Asn Gly
            210                 215                 220
His Ser Phe Pro Pro Thr Phe Gly Gly Gly Thr Lys Val Glu Ile Lys
225                 230                 235                 240

<210> SEQ ID NO 7
<211> LENGTH: 63
<212> TYPE: DNA
<213> ORGANISM: Homo sapiens

<400> SEQUENCE: 7
atggccttac cagtgaccgc cttgctcctg ccgctggcct tgctgctcca cgccgccagg   60
ccg                                                                63

<210> SEQ ID NO 8
<211> LENGTH: 21
<212> TYPE: PRT
<213> ORGANISM: Homo sapiens

<400> SEQUENCE: 8

Met Ala Leu Pro Val Thr Ala Leu Leu Leu Pro Leu Ala Leu Leu Leu
1               5                   10                  15

His Ala Ala Arg Pro
            20

<210> SEQ ID NO 9
<211> LENGTH: 141
<212> TYPE: DNA
<213> ORGANISM: Homo sapiens

<400> SEQUENCE: 9
aagcccacca cgacgccagc gccgcgacca ccaacaccgg cgcccaccat cgcgtcgcag   60
cccctgtccc tgcgcccaga ggcgagccgg ccagcggcgg ggggcgcagt gcacacgagg  120
gggctggact cgccagtga t                                             141

<210> SEQ ID NO 10
<211> LENGTH: 47
<212> TYPE: PRT
<213> ORGANISM: Homo sapiens

<400> SEQUENCE: 10

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30
```

```
Ala Gly Gly Ala Val His Thr Arg Gly Leu Asp Phe Ala Ser Asp
        35                  40                  45

<210> SEQ ID NO 11
<211> LENGTH: 81
<212> TYPE: DNA
<213> ORGANISM: Homo sapiens

<400> SEQUENCE: 11
ttttgggtgc tggtggtggt tggtggagtc ctggcttgct atagcttgct agtaacagtg      60
gcctttatta ttttctgggt g                                                81

<210> SEQ ID NO 12
<211> LENGTH: 27
<212> TYPE: PRT
<213> ORGANISM: Homo sapiens

<400> SEQUENCE: 12

Phe Trp Val Leu Val Val Val Gly Gly Val Leu Ala Cys Tyr Ser Leu
 1               5                  10                  15

Leu Val Thr Val Ala Phe Ile Ile Phe Trp Val
            20                  25

<210> SEQ ID NO 13
<211> LENGTH: 123
<212> TYPE: DNA
<213> ORGANISM: Homo sapiens

<400> SEQUENCE: 13
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                   123

<210> SEQ ID NO 14
<211> LENGTH: 41
<212> TYPE: PRT
<213> ORGANISM: Homo sapiens

<400> SEQUENCE: 14

Arg Ser Lys Arg Ser Arg Leu Leu His Ser Asp Tyr Met Asn Met Thr
 1               5                  10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 15
<211> LENGTH: 345
<212> TYPE: DNA
<213> ORGANISM: Homo sapiens

<400> SEQUENCE: 15
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgcag agaaggaaga accctcagga aggcctgtac     180
aatgaactgc agaaagataa gatggcggag gcctacagtg agattgggat gaaaggcgag     240
cgccggaggg gcaaggggca cgatggcctt taccagggtc tcagtacagc caccaaggac     300
```
acctacgacg cccttcacat gcaggccctg cccctcgct aatag 345

<210> SEQ ID NO 16
<211> LENGTH: 113
<212> TYPE: PRT
<213> ORGANISM: Homo sapiens

<400> SEQUENCE: 16

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 17
<211> LENGTH: 495
<212> TYPE: PRT
<213> ORGANISM: Homo sapiens

<400> SEQUENCE: 17

Met Ala Leu Pro Val Thr Ala Leu Leu Leu Pro Leu Ala Leu Leu Leu
1               5                   10                  15

His Ala Ala Arg Pro Ala Ser Gln Val Gln Leu Val Gln Ser Gly Ala
            20                  25                  30

Glu Val Lys Lys Pro Gly Ser Ser Val Lys Val Ser Cys Lys Ala Ser
        35                  40                  45

Gly Tyr Thr Phe Thr Ser Tyr Val Met His Trp Val Arg Gln Ala Pro
    50                  55                  60

Gly Gln Gly Leu Glu Trp Met Gly Tyr Ile Ile Pro Tyr Asn Asp Ala
65                  70                  75                  80

Thr Lys Tyr Asn Glu Lys Phe Lys Gly Arg Val Thr Ile Thr Ala Asp
                85                  90                  95

Lys Ser Thr Ser Thr Ala Tyr Met Glu Leu Ser Ser Leu Arg Ser Glu
            100                 105                 110

Asp Thr Ala Val Tyr Tyr Cys Ala Arg Tyr Asn Tyr Asp Gly Tyr Phe
        115                 120                 125

Asp Val Trp Gly Gln Gly Thr Leu Val Thr Val Ser Ser Gly Gly Gly
    130                 135                 140

Gly Ser Gly Gly Gly Ser Gly Gly Gly Ser Glu Ile Val Leu
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Ser Ile Ser Asp Tyr Leu His Trp Tyr
            180                 185                 190

Gln Gln Lys Pro Gly Gln Ala Pro Arg Leu Leu Ile Tyr Tyr Ala Ser
        195                 200                 205

```
Gln Ser Ile Thr Gly Ile Pro Ala Arg Phe Ser Gly Ser Gly Ser Gly
    210                 215                 220

Thr Asp Phe Thr Leu Thr Ile Ser Ser Leu Glu Pro Glu Asp Phe Ala
225                 230                 235                 240

Val Tyr Tyr Cys Gln Asn Gly His Ser Phe Pro Pro Thr Phe Gly Gly
                245                 250                 255

Gly Thr Lys Val Glu Ile Lys Leu Glu Lys Pro Thr Thr Thr Pro Ala
                260                 265                 270

Pro Arg Pro Pro Thr Pro Ala Pro Thr Ile Ala Ser Gln Pro Leu Ser
            275                 280                 285

Leu Arg Pro Glu Ala Ser Arg Pro Ala Ala Gly Gly Ala Val His Thr
        290                 295                 300

Arg Gly Leu Asp Phe Ala Ser Asp Lys Pro Phe Trp Val Leu Val Val
305                 310                 315                 320

Val Gly Gly Val Leu Ala Cys Tyr Ser Leu Leu Val Thr Val Ala Phe
                325                 330                 335

Ile Ile Phe Trp Val Arg Ser Lys Arg Ser Arg Leu Leu His Ser Asp
                340                 345                 350

Tyr Met Asn Met Thr Pro Arg Arg Pro Gly Pro Thr Arg Lys His Tyr
        355                 360                 365

Gln Pro Tyr Ala Pro Pro Arg Asp Phe Ala Ala Tyr Arg Ser Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Gln
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495
```